US008383860B2

(12) United States Patent
Cook et al.

(10) Patent No.: US 8,383,860 B2
(45) Date of Patent: *Feb. 26, 2013

(54) PROCESS TO SELECTIVELY MANUFACTURE DIETHYLENETRIAMINE (DETA) OR OTHER DESIRABLE ETHYLENEAMINES VIA CONTINUOUS TRANSAMINATION OF ETHYLENEDIAMINE (EDA), AND OTHER ETHYLENEAMINES OVER A HETEROGENEOUS CATALYST SYSTEM (75) Inventors: Ronald G. Cook, Hurricane, WV (US); Stephen W. King, League City, TX (US); David M. Petraitis, Covington, LA (US); Thomas Z. Smak, Arlington Heights, IL (US)

(73) Assignee: Union Carbide Chemicals & Plastics Technology LLC, Midland, MI (US)

( * ) Notice: Subject to any disclaimer, the term of this patent is extended or adjusted under 35 U.S.C. 154(b) by 461 days.

This patent is subject to a terminal disclaimer.

(21) Appl. No.: 12/587,372

(22) Filed: Oct. 6, 2009

(65) Prior Publication Data

US 2010/0087683 A1   Apr. 8, 2010

Related U.S. Application Data (60) Provisional application No. 61/195,404, filed on Oct. 6, 2008.

(51) Int. Cl.
*C07C 209/00* (2006.01)
(52) U.S. Cl. .......................... 564/470; 544/358; 544/382
(58) Field of Classification Search ........................ None
See application file for complete search history.

(56) References Cited

U.S. PATENT DOCUMENTS

| 2,861,995 | A | 11/1958 | MacKenzie |
| 3,110,732 | A | 11/1963 | Speranza et al. |
| 3,394,186 | A | 7/1968 | Muhlbauer |
| 3,658,692 | A | 4/1972 | Gilbert et al. |
| 3,847,754 | A | 11/1974 | Oliver |
| 4,032,411 | A | 6/1977 | Tornquist et al. |
| 4,073,750 | A | 2/1978 | Yates et al. |
| 4,111,840 | A | 9/1978 | Best |
| 4,123,462 | A | 10/1978 | Best |
| 4,209,424 | A | 6/1980 | Le Goff et al. |
| 4,264,776 | A | 4/1981 | Hershman et al. |
| 4,328,370 | A | 5/1982 | Fazio |
| 4,400,539 | A | 8/1983 | Gibson et al. |
| 4,404,405 | A | 9/1983 | Winters |
| 4,510,263 | A | 4/1985 | Pereira et al. |
| 4,552,961 | A | 11/1985 | Herdle |
| 4,568,746 | A | 2/1986 | Cowherd, III |
| 4,584,405 | A | 4/1986 | Vanderpool |
| 4,602,091 | A | 7/1986 | Brennan |
| 4,708,945 | A | 11/1987 | Murrell et al. |
| 4,729,981 | A | 3/1988 | Kobylinski et al. |
| 4,801,573 | A | 1/1989 | Eri et al. |
| 4,806,517 | A | 2/1989 | Vanderpool et al. |
| 4,845,296 | A | 7/1989 | Ahmed et al. |
| 4,870,044 | A | 9/1989 | Kukes et al. |
| 4,883,826 | A | 11/1989 | Marugg et al. |
| 4,888,316 | A | 12/1989 | Gardner et al. |
| 4,906,782 | A | 3/1990 | Hara et al. |
| 4,922,024 | A | 5/1990 | Bowman et al. |
| 4,927,931 | A | 5/1990 | Molzahn et al. |
| 4,983,735 | A | 1/1991 | Hartwell et al. |
| 5,030,740 | A | 7/1991 | Bowman et al. |
| 5,073,635 | A | 12/1991 | Bowman et al. |
| 5,120,815 | A | 6/1992 | Marugg et al. |
| 5,166,442 | A | 11/1992 | Hartwell et al. |
| 5,225,599 | A | 7/1993 | King et al. |
| 5,225,600 | A | 7/1993 | King et al. |
| 5,248,827 | A | 9/1993 | Hara et al. |
| 5,256,786 | A | 10/1993 | Bowman et al. |
| 5,288,909 | A | 2/1994 | Hartwell et al. |
| 5,321,160 | A | 6/1994 | Hironaka et al. |
| 5,352,835 | A | 10/1994 | Dai et al. |
| 5,410,087 | A | 4/1995 | Hartwell et al. |
| H1447 | H | 6/1995 | Linton |
| 5,455,352 | A | 10/1995 | Huellmann et al. |
| 5,552,363 | A | 9/1996 | Pannell et al. |
| 5,554,793 | A | 9/1996 | Hartwell et al. |
| 5,721,305 | A | 2/1998 | Eshuis et al. |
| 5,750,790 | A | 5/1998 | King |
| 5,851,948 | A | 12/1998 | Chuang et al. |
| 5,935,889 | A | 8/1999 | Murrell et al. |
| 6,117,814 | A | 9/2000 | Plecha et al. |

(Continued)

FOREIGN PATENT DOCUMENTS

| EP | 0 163 253 | 12/1985 |
| EP | 0 197 612 | 10/1986 |

(Continued)

OTHER PUBLICATIONS

Database Caplus [Online] Chemical Abstracts Service, Columbus, Ohio, US; 2005, Kiebach, Ragnar et al.: "Solvothermal synthesis of [C6H17N3] Sb10S16: A new thioantimonate(III) with an in-situ formed organic amine cation," XP002562885 retrieved from STN Database accession No. 2005: 168744 Abstract & Zeitschrift für Naturforschung, B: 2004, 59 (11/12), 1314-1319.

Komiyama et al., "Concentration Profiles in Impregnation of Porous Catalysts: Nickel on Alumina," Journal of Catalysis, vol. 63, School of Chemical Engineering, Cornell University, and Chevron Research Company, pp. 35-52 (1980).

Database Beilstein [Online] Beilstein Institute for Organic Chemistry, Frankfurt-Main, DE; 1951, XP002576591, Database accession No. 845679 (reaction ID) abstract & Jur'ew, Lewi: Doklady Akademii Nauk SSSR, vol. 78, 1951, pp. 725-727, ISSN: 0002-3264. Zagidullin, Abstract, "Simultaneous manufacture of acyclic and cyclic di- and polyethylenepolyamines," Khimicheskaya Promyshlennost, (1987).

(Continued)

*Primary Examiner* — Brian J Davis
(74) *Attorney, Agent, or Firm* — Kagan Binder, PLLC (57) ABSTRACT

The present invention reacts ethylenediamine with one or more additional ethyleneamines in the presence of a transamination catalyst to provide a different, preferably more desirable product mix of one or more ethyleneamines.

16 Claims, 1 Drawing Sheet

U.S. PATENT DOCUMENTS

| | | | |
|---|---|---|---|
| 6,124,367 | A | 9/2000 | Plecha et al. |
| 6,169,207 | B1 | 1/2001 | Tsuneki et al. |
| 6,222,008 | B1 | 4/2001 | Gelles |
| 6,235,677 | B1 | 5/2001 | Manzer et al. |
| 6,306,795 | B1 | 10/2001 | Ryan et al. |
| 6,465,530 | B2 | 10/2002 | Roy-Auberger et al. |
| 6,469,214 | B2 | 10/2002 | Melder et al. |
| 6,534,441 | B1 | 3/2003 | Bartley et al. |
| 6,576,796 | B1 | 6/2003 | Funke et al. |
| 6,703,343 | B2 | 3/2004 | Park |
| 6,977,273 | B2 | 12/2005 | Roy-Auberger et al. |
| 7,045,485 | B2 | 5/2006 | Kelkar et al. |
| 7,053,246 | B2 | 5/2006 | Gerlach et al. |
| 7,053,247 | B2 | 5/2006 | Lif et al. |
| 7,056,857 | B2 | 6/2006 | Srinivasan et al. |
| 7,067,455 | B2 | 6/2006 | Chen et al. |
| 7,256,154 | B2 | 8/2007 | Moon et al. |
| 7,323,100 | B2 | 1/2008 | Espinoza et al. |
| 7,341,976 | B2 | 3/2008 | Espinoza et al. |
| 7,348,293 | B2 | 3/2008 | Timken |
| 7,393,978 | B2 | 7/2008 | Frauenkron et al. |
| 7,541,310 | B2 | 6/2009 | Espinoza et al. |
| 7,595,276 | B2 | 9/2009 | Kodama et al. |
| 7,745,369 | B2 | 6/2010 | Bhan et al. |
| 7,769,619 | B1 | 8/2010 | Krysinski et al. |
| 7,824,656 | B2 | 11/2010 | Idem et al. |
| 7,981,836 | B2 | 7/2011 | Kanazirev et al. |
| 2003/0013873 | A1 | 1/2003 | Neumann et al. |
| 2004/0171884 | A1* | 9/2004 | Lif et al. ............. 564/470 |
| 2005/0095189 | A1 | 5/2005 | Brey et al. |
| 2006/0030726 | A1 | 2/2006 | Telschow |
| 2006/0276649 | A1* | 12/2006 | Frauenkron et al. ......... 544/358 |
| 2007/0100144 | A1 | 5/2007 | Frauenkron et al. |
| 2008/0003131 | A1 | 1/2008 | Bauer et al. |
| 2010/0056366 | A1 | 3/2010 | Lee |
| 2010/0087685 | A1 | 4/2010 | King et al. |
| 2010/0094008 | A1 | 4/2010 | King et al. |

FOREIGN PATENT DOCUMENTS

| | | |
|---|---|---|
| EP | 0197611 | 10/1986 |
| EP | 0 254 335 | 1/1988 |
| EP | 0 284 398 | 9/1988 |
| EP | 0 526 851 | 2/1993 |
| EP | 0075940 | 9/1994 |
| EP | 0 737 669 | 10/1996 |
| EP | 1 211 238 | 6/2002 |
| EP | 1 249 440 | 10/2002 |
| GB | 1508460 | 4/1978 |
| IL | 57019 | 9/1983 |
| JP | 05 09777 | 4/1993 |
| RU | 2 186 761 | 8/2002 |
| RU | 2 226 188 | 3/2004 |
| RU | 2 226 189 | 3/2004 |
| WO | WO 99/24389 | 5/1999 |
| WO | WO 01/44150 | 6/2001 |
| WO | WO 01/66247 | 9/2001 |
| WO | WO 01/98243 | 12/2001 |
| WO | WO 03/010125 | 2/2003 |
| WO | WO 2005/012223 | 2/2005 |
| WO | WO 2005/014523 | 2/2005 |
| WO | WO 2005/061430 | 7/2005 |
| WO | WO 2006/053342 | 5/2006 |
| WO | WO 2006/060206 | 6/2006 |
| WO | WO 2006/114417 | 11/2006 |
| WO | WO 2007/093514 | 8/2007 |
| WO | WO 2008/104582 | 9/2008 |
| WO | WO 2009/083580 | 7/2009 |

OTHER PUBLICATIONS

Reichle, "Reactions of Aliphatic α-ω- Diamines in H+-Pentasils," Journal of Catalysis, vol. 144, Union Carbide Chemicals and Plastics Company, Inc., Specialty Chemicals Division, pp. 556-568 (1993).

Tanabe et al., "A New Hypothesis Regarding the Surface Acidity of Binary Metal Oxides," Bulletin of the Chemical Society of Japan, vol. 47, Department of Chemistry, Faculty of Science, Hokkaido University, pp. 1064-1066 (1974).

Fluid Phase Equilibria, Olson, James D., Thermodynamics of hydrogen-bonding mixtures 4: $G^E$, $H^E$, $S^E$ and $C^E_p$ and possible double azeotropy of water + N-methylethylenediamine, vol. 185, p. 209-218, (2001).

* cited by examiner

PROCESS TO SELECTIVELY MANUFACTURE DIETHYLENETRIAMINE (DETA) OR OTHER DESIRABLE ETHYLENEAMINES VIA CONTINUOUS TRANSAMINATION OF ETHYLENEDIAMINE (EDA), AND OTHER ETHYLENEAMINES OVER A HETEROGENEOUS CATALYST SYSTEM

PRIORITY CLAIM

The present non-provisional patent Application claims priority under 35 U.S.C. §119(e) from United States Provisional patent application having Ser. No. 61/195,404 filed on Oct. 6, 2008, by Cook et al. and entitled "A PROCESS TO SELECTIVELY MANUFACTURE DIETHYLENETRIAMINE (DETA) OR OTHER DESIRABLE ETHYLENEAMINES VIA CONTINUOUS TRANSAMINATION OF ETHYLENEDIAMINE (EDA), AND OTHER ETHYLENEAMINES OVER A HETEROGENEOUS CATALYST SYSTEM," which application is incorporated herein by reference in its entirety.

FIELD OF THE INVENTION

The present invention relates to manufacturing one or more ethyleneamines by subjecting one or more ethyleneamines to a transamination reaction.

BACKGROUND OF THE INVENTION

Methods of making ethyleneamines via transamination are known. See, e.g., U.S. Pat. Nos. 7,053,247 (Lif et al.) and 7,393,978 (Frauenkron et al.), U.S. Publication Number 2007/0100144 (Frauenkron et al.), and GB 1508460.

U.S. Pat. No. 7,053,247 (Lif et al.) relates to a process for the manufacture of diethylenetriamine and higher polyethylenepolyamines by a transamination of ethylenediamine.

U.S. Pat. No. 7,393,978 (Frauenkron et al.) relates to a process for the preparation of ethyleneamines, in particular diethylenetriamine (DETA), by continuous reaction of ethylenediamine (EDA) in the presence of a heterogeneous catalyst, where the reaction is carried out in a reaction column.

U.S. Publication Number 2007/0100144 (Frauenkron et al.), relates to the preparation of ethyleneamines by reacting monoethanolamine (MEOA) with ammonia in the presence of a catalyst in a reactor and separating the resulting reaction product, where ethylenediamine (EDA) obtained in the separation is reacted in a separate reactor in the presence of a catalyst to give diethylenetriamine (DETA), and the resulting reaction product is passed to the separation of the reaction product resulting from the first reactor.

There is still a need for improved processes that make ethyleneamines via transamination. For example, many transamination processes have a limited selectivity towards the product mix of ethyleneamines that is produced. If the selectivity does not at least closely match market demand, the process tends to be inefficient because more of an undesired product is typically made so as to produce a quantity of desired ethyleneamine. Improved selectivity of the ethyleneamine product mix could allow production to be tailored to market demand so as to improve operating costs and the like.

SUMMARY OF THE INVENTION

The present invention reacts ethylenediamine with one or more additional ethyleneamines in the presence of a transamination catalyst to provide one or more ethyleneamines. The selectivity of the transamination reaction can be controlled to produce a desired ethyleneamine product based on a given transamination feed stream and operating conditions. Advantageously, a relatively less desirable ethyleneamine product mix (e.g., coming from a relatively less controllable ethyleneamine production process such as reductive amination) can be converted into a more desirable ethylene product mix by subjecting the less desirable ethyleneamine product mix to a transamination process according to the present invention. So as market demands for particular ethyleneamine(s) changes, a process according to the present invention can use a less desirable mix of ethyleneamine(s) and produce a more desirable/valuable product mix of ethyleneamines that maximizes the amount of desirable ethyleneamine(s) produced and minimizes the amount of less desirable ethyleneamines. As another advantage, the process can be implemented as a stand alone/modular facility or integrated into an existing ethyleneamines unit.

According to one aspect of the present invention, a process for the manufacture of one or more ethyleneamines by a transamination reaction, includes the step of reacting ethylenediamine with one or more additional ethyleneamines in the presence of a transamination catalyst to provide the one or more ethyleneamines. The one or more additional ethyleneamines are selected from the group consisting of: diethylenetriamine, triethylenetetramine, tetraethylenepentamine, aminoethylethanolamine, aminoethylpiperazine, piperazinoethylethylenediamine, heavy polyamine and combinations thereof.

According to another aspect of the present invention, a process for the manufacture of one or more ethyleneamines by a transamination reaction includes the step of reacting a first mixture in the presence of a transamination catalyst to provide a second mixture. The first mixture comprises ethylenediamine and one or more additional ethyleneamines. The one or more additional ethyleneamines are selected from the group consisting of: diethylenetriamine, triethylenetetramine, tetraethylenepentamine, aminoethylethanolamine, aminoethylpiperazine, piperazinoethylethylenediamine, heavy polyamine and combinations thereof. At least two ethyleneamines in the first mixture are present in an amount that is different than the amount of the corresponding two ethyleneamines in the second mixture.

According to another aspect of the present invention, a process for the manufacture of one or more ethyleneamines by a transamination reaction includes the step of reacting ethylenediamine with one or more additional ethyleneamines in the presence of a transamination catalyst in a fixed bed reactor to provide the one or more ethyleneamines.

According to another aspect of the present invention, a process for the manufacture of one or more ethyleneamines by a transamination reaction includes the step of reacting ethylenediamine in the presence of a transamination catalyst to provide the one or more ethyleneamines. The catalyst includes a) a support portion having an acidic mixed metal oxide including a transitional alumina and a second metal oxide, wherein the second metal oxide has a weight percentage that is less than the weight percentage of alumina; and b) a catalyst portion having one or more metals selected from the group consisting of cobalt, nickel, and copper, wherein there is no, or less than 0.01 wt. % rhenium in the catalyst, and the catalyst portion is 25 wt. % or less of the catalyst.

According to another aspect of the present invention, a process for the manufacture of one or more ethyleneamines by a transamination reaction, includes the step of reacting ethylenediamine in the presence of a transamination catalyst to provide the one or more ethyleneamines. The catalyst includes a) a support portion comprising an acidic mixed metal oxide comprising a transitional alumina and a second metal oxide; and b) a catalyst portion comprising nickel and rhenium, wherein: the second metal oxide has a weight percentage that is less than the weight percentage of alumina, the catalyst portion is 25 weight percent or less of the catalyst composition, the catalyst portion comprises nickel in an amount in the range of 2 to 20 weight percent, based upon total catalyst composition weight, and there is no boron in the catalyst portion.

According to another aspect of the present invention, a modular reaction system for the manufacture of one or more ethyleneamines by a transamination reaction includes: a) a reactor comprising a transamination catalyst; and b) program instructions to cause ethylenediamine to react with one or more additional ethyleneamines in the presence of the transamination catalyst to provide the one or more ethyleneamines.

BRIEF DESCRIPTION OF THE DRAWINGS

The advantages of the present invention, and the manner of attaining them, will become more apparent and the invention itself will be better understood by reference to the following description of the embodiments of the invention taken in conjunction with the accompanying drawing, wherein.

DETAILED DESCRIPTION

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

All publications and patents mentioned herein are incorporated herein by reference in their respective entireties for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventor is not entitled to antedate such disclosure by virtue of prior invention.

A process for the manufacture of one or more ethyleneamines according to the present invention uses a feed of one or more ethyleneamines for a transamination reaction.

Ethyleneamines that can be used in a process according to the present invention are well known and can include one or more of ethylenediamine (EDA), diethylenetriamine (DETA), triethylenetetramine (TETA), tetraethylenepentamine (TEPA), piperazine (PIP), aminoethylpiperazine (AEP), aminoethylethanolamine (AEEA), piperazinoethylethylenediamine (PEEDA), heavy polyamine (HPA), and combinations thereof. HPA is a mixture of linear, branched, and/or cyclic ethyleneamines, the structures of which can be deduced from the chemistry of manufacture and knowledge of the structures present in TETA and TEPA. The structures of the principle components of HPA can contain six or more nitrogen atoms per molecule.

The amount of one or more ethyleneamines after the transamination reaction is controllably different than the amount of the corresponding ethyleneamine(s) before the transamination reaction. Advantageously, a relatively less desirable ethyleneamine product mix (e.g., coming from a relatively less controllable ethyleneamine production process such as reductive amination) can be transformed into a more desirable ethyleneamine product mix by subjecting the less desirable ethyleneamine product mix to a transamination process according to the present invention. For example, a process according to the present invention can subject a reactant mixture that has a relatively high amount of one or more ethyleneamines other than diethylenetriamine (DETA), and produce a product mixture that is relatively high in DETA. For example, a reactant mixture could have relatively high amounts of ethylenediamine (EDA) or EDA and piperazine (PIP), while the product mixture produced according to the invention could be relatively high in DETA. As another example, a product mix that is relatively high in amounts of the oligomers triethylenetetramine (TETA) and tetraethylenepentamine (TEPA) can be produced by subjecting a feed that is relatively high in amounts of EDA and/or DETA to a transamination reaction according to the present invention. In certain embodiments, desirable ethyleneamine product mixes can be produced according to the present invention with relatively little or no amino ethylethanolamine (AEEA) produced as a co-product and lower amounts of undesirable cyclic ethyleneamines relative to the desired ethyleneamines.

The source of the one or more ethyleneamines that are subjected to a transamination reaction according to present invention can be raw materials, materials delivered from an upstream process (e.g., an upstream process or processes that makes the ethyleneamine(s) such as reductive amination, ethylene dichloride and ammonia, and condensations), or a combination of these. For example, in certain embodiments, one or more ethyleneamines that are produced in a reductive amination reaction can be used as feed for a transamination process according to the present invention. See U.S. Provisional Patent Application titled "METHOD OF MANUFACTURING ETHYLENEAMINES" by David M. Petraitis et al., having Ser. No. 61/195,454, and filed on Oct. 6, 2008, the entirety of which reference is incorporated herein by reference. See also, U.S. Provisional Patent Application titled "METHODS FOR MAKING ETHANOLAMINE(S) AND ETHYLENEAMINE(S) FROM ETHYLENE OXIDE AND AMMONIA, AND RELATED METHODS" by David Do et al., having Ser. No. 61/195,405, and filed on Oct.6, 2008, the entirety of which reference is incorporated herein by reference. Transamination is a transfer of an amino group from one chemical compound to another, or the transposition of an amino group within a chemical compound. Transamination is also disclosed in U.S. Provisional Patent Application titled "METHODS OF MAKING CYCLIC, N-AMINO FUNCTIONAL TRIAMINES" by Stephen W. King, having Ser. No. 61/195,412, and filed on Oct.6, 2008, the entirety of which reference is incorporated herein by reference.

Optionally, one or more additional components can be combined with the ethyleneamine reactants prior to and/or within the transamination reactor. For example ammonia ($NH_3$) can be included in the transamination feed stream to minimize the extent of unfavorable reaction(s). As another example, hydrogen can be included in the transamination feed stream in an amount sufficient to affect catalyst activity and product selectivity. Exemplary amounts of hydrogen include 0.001 to 10.0 mole % based on liquid feed.

The transamination reaction can be practiced in any suitable reactor. These include batch reactor, continuous fixed bed reactors, slurry bed reactors, fluidized bed reactors, catalytic distillation reactors, combinations of these, and the like. In certain embodiments, a fixed bed reactor is preferred. A fixed bed reactor includes catalyst pellets that are held in place and do not substantially move with respect to fixed reference frame. At least a portion of the reactor feed material passes over (flows past) the catalyst pellets and reacts to form product(s).

The reactor conditions can be set so as to form a desired product mix given the reactor feed and catalyst(s) used. Preferably, the reactor conditions are relatively moderate so as to reduce operating costs and the like. A preferred transamination reaction temperature can be a temperature in the range of from 130° C.-180° C., preferably in the range of from 130° C.-170° C., even more preferably in the range of from 130° C.-160° C. A preferred transamination reaction pressure can be a pressure in the range of from 200-2000 psig. A preferred transamination reaction reactor space velocity can be in the range of from 5-50 gram moles of ethyleneamines per kilogram of catalyst per hour.

In preferred embodiments, a transamination reaction according to the present invention can have feed conversions of 25% or more, e.g., in the range of from 25% to 65%.

Any catalyst that can catalyze a transamination reaction can be used in a process according to the present invention. Such catalysts are well known. A preferred catalyst includes a hydrogenation catalyst or dehydrogenation catalyst. A hydrogenation catalyst can be made of nickel (Ni), copper (Cu), cobalt (Co), ruthenium (Ru), rhenium (Re), rhodium (Rh), platinum (Pt), palladium (Pd), and combinations thereof. Any catalyst support that can support a catalyst for a transamination reaction can be used in a process according to the present invention. Catalyst supports are well known and include, e.g., metal oxide. In preferred embodiments, a mixed metal oxide is used, and more preferably a transitional alumina containing silica is used.

One preferred catalyst includes nickel and rhenium as described in U.S. Provisional Patent Application titled "LOW METAL CATALYST COMPOSITIONS INCLUDING ACIDIC MIXED METAL OXIDE AS SUPPORT" by Stephen W. King et al., having Ser. No. 61/195,455, and filed on Oct.6, 2008, the entirety of which reference is incorporated herein by reference. And yet another preferred combination includes nickel, cobalt, or copper, or combinations thereof as described in U.S. Provisional Patent Application titled "LOW METAL LOADED, ALUMINA SUPPORTED, CATALYST COMPOSITIONS AND AMINATION PROCESS" by Stephen W. King et al., having Ser. No. 61/195,434, and filed on Oct.6, 2008, the entirety of which reference is incorporated herein by reference. Such catalysts show significantly improved selectivity to ethylenediamine. Advantageously, such catalyst can achieve much improved selectivity at relatively moderate temperature and pressure conditions. For example, such catalyst can achieve the desired product selectivity at a temperature in the range of from 110° C. to 180° C., preferably from 130° C. to 160° C., and a pressure of 2000 psig or less.

One or more ammonia recovery systems can be used in the process of making ethyleneamines according to the present invention. An ammonia recovery system separates ammonia, and optionally one or more additional components (e.g., hydrogen), from a fluid stream. An ammonia recovery system can be positioned anywhere in the overall process as desired. Preferably, one or more ammonia recovery systems are used in a manner that minimizes the number of ammonia recovery systems and/or other process units. The recovered ammonia can be used in any desired manner. For example, depending on the purity level of the recovered ammonia, the recovered ammonia may be recycled to another point in the process such as the inlet of a reactor. Advantageously, such recovered ammonia can be used as "make-up" ammonia for a reactor where ammonia is consumed in a reaction.

Ammonia recovery systems can be any type of ammonia recovery system known in the art. For example, an ammonia recovery system can utilize distillation columns, multiple single stage separators, compressors, chillers and/or absorbers in many different combinations and the like.

The one or more ethyleneamines made by a process according to the present invention can be separated and recovered by any method known in the art. For example, the ethyleneamines can be refined using conventional distillation technology known in the art. Preferably, dividing wall columns are used.

Other separation techniques can include (membranes, melt crystallization, reactive distillation).

A transamination process according to the present invention can be used in a stand alone (modular) system or it can be integrated with a larger system that makes one or more ethyleneamines which could be used as a feed for the transamination process according to the present invention. As used herein, a "modular" reaction system for the manufacture of one or more ethyleneamines by a transamination reaction means a stand alone system that can have EDA and other ethyleneamines introduced directly as raw feed or a stand alone system that has been integrated into a larger system (e.g., an existing system) and can have EDA and other ethyleneamines introduced from an upstream process. Larger systems into which a modular transamination reaction system according to the present invention could be integrated into include systems that can produce one or more ethyleneamines such as an ethylene dichloride (EDC) based system, a condensation based system, and/or a reductive animation based system. An example of the present invention integrated into a reductive amination system is further described in U.S. Provisional Patent Application titled "METHOD OF MANUFACTURING ETHYLENEAMINES" by David M. Petraitis et al., having Ser. No. 61/195,454, and filed on Oct.6, 2008, the entirety of which reference is incorporated herein by reference. See also, U.S. Provisional Patent Application titled "METHODS FOR MAKING ETHANOLAMINE(S) AND ETHYLENEAMINE(S) FROM ETHYLENE OXIDE AND AMMONIA, AND RELATED METHODS" by David Do et al., having Ser. No. 61/195,405, and filed on Oct. 6, 2008, the entirety of which reference is incorporated herein by reference.

Advantageously, because of the relatively high selectivity of ethyleneamine product mix that can be achieved by a process according to the present invention, a modular transamination system according to the present invention can be incorporated (e.g., retrofitted) with other systems (e.g., reductive amination systems) such that the feed for the transamination system comes from one or more upstream processes that may not have such desirable selectivity in the ethyleneamines product mix. Preferably, a modular system has its own refining train. Also, such a modular system can include a processing unit such as a computer or the like to carry out program instructions (e.g., programming code) of a process according to the present invention.

The present invention will now be further illustrated by reference to the exemplary schematic flow diagram shown in FIG. 1.

Figure 1:
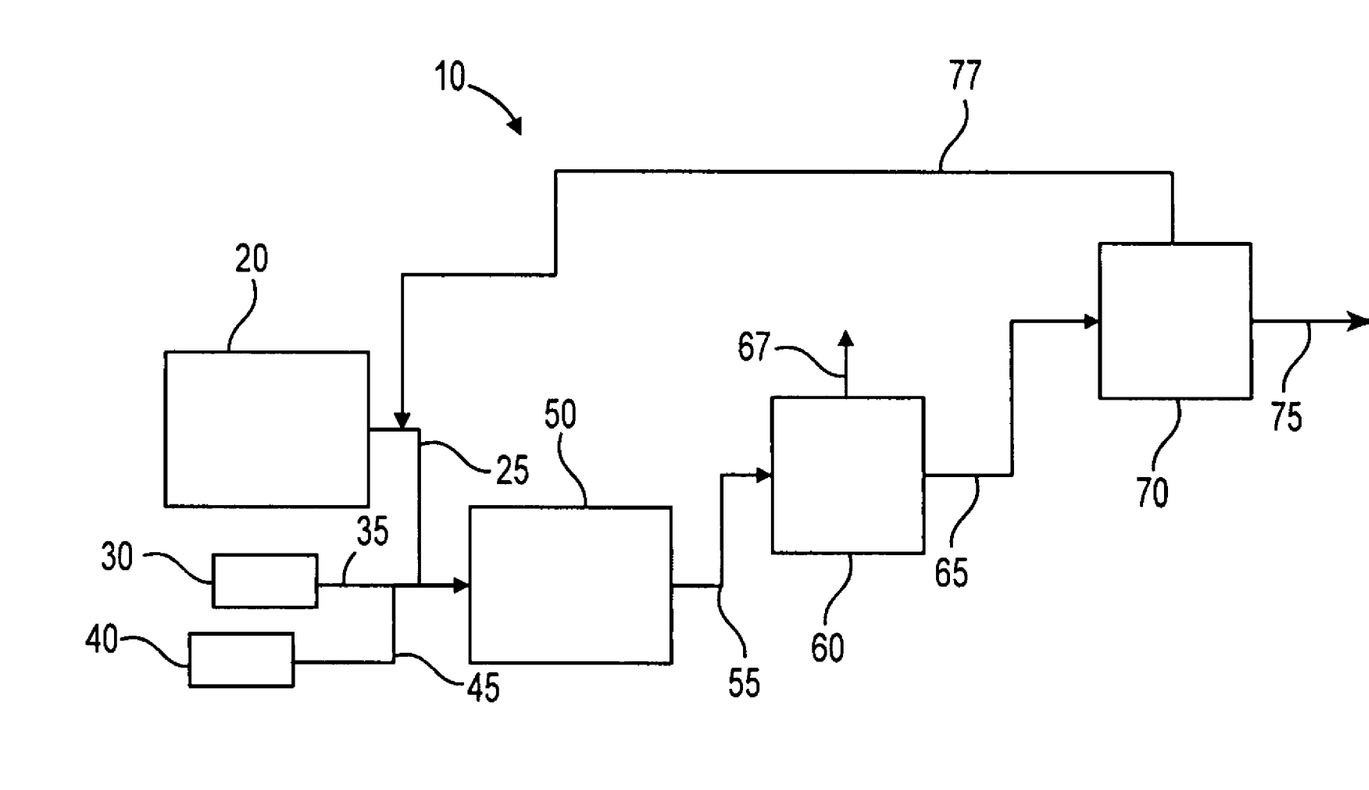
FIG. 1—is a block diagram schematically illustrating a process according to the present invention for the preparation of one or more ethyleneamines by a transamination reaction.

FIG. 1 shows a block diagram schematically illustrating a process 10 according to the present invention for the preparation of one or more ethyleneamines by a transamination reaction. A source of one or more ethyleneamines 20 is fed to a transamination reactor 50 via stream 25. The source 20 of ethyleneamines can include ethylenediamine (EDA), diethylenetriamine (DETA), triethylenetetramine (TETA), tetraethylenepentamine (TEPA), piperazine (PIP), aminoethylpiperazine (AEP), and heavy polyamine (HPA), or mixtures thereof. As shown, a source of hydrogen gas 30 and a source of ammonia 40 can optionally be combined with the ethyleneamines from source 20 and fed to reactor 50 via lines 35 and 45, respectively. As shown, reactor 50 produces an effluent having a product mix of ethyleneamines that include ethylenediamine (EDA), diethylenetriamine (DETA), triethylenetetramine (TETA), tetraethylenepentamine (TEPA), piperazine (PIP), aminoethylpiperazine (AEP), and heavy polyamine (HPA). The amount of each ethyleneamine coming out of reactor 50 is controllably different than the amount of each ethyleneamine going into reactor 50 because of how the transamination reaction is performed. Advantageously, a relatively less desirable ethyleneamine product mix (e.g., coming from a relatively less controllable ethyleneamine production process such as reductive amination) can be transformed into a more desirable ethyleneamines product mix by subjecting the less desirable ethyleneamines product mix to a transamination process according to the present invention. The effluent from reactor 50 is fed to ammonia recovery unit 60 via line 55. Ammonia recovery unit 60 separates ammonia from the ethyleneamines and sends the ammonia overhead via line 67. The ethyleneamines are sent to product refining system 70 via line 65 where the ethyleneamines can be separated into individual ethyleneamine species. Optionally, one or more ethyleneamines that are separated in product refining system 70 can be combined with the ethyleneamines from source 20 via stream 77 and fed to reactor 50.

EXAMPLES

Catalyst Preparation

The catalysts used in the Examples 1-5 below were prepared as described below. Precursor salts of the Nickel (Ni) and Rhenium (Re) were dissolved in 70-80° C. water to form an impregnation solution. The final volume of the impregnation solution was adjusted to equal the adsorption volume required for the number of times that the carrier was impregnated, and the quantities of the precursor salts were those calculated to give the metal compositions provided in the examples. In each case the carrier was impregnated to incipient wetness by the addition of the appropriate amount of impregnation solution and gently agitated until all the liquid was adsorbed. The sample was then placed in a muffle furnace and calcined in air for one hour at 340° C. When the support had cooled, additional impregnations were performed until all of the solution had been added. A calcination step at 340° C. was done after each impregnation. Prior to use, the catalyst compositions were reduced in hydrogen by ramping the temperature at 3° C./min to 230° C., holding at 230° C. for one hour, and then ramping at 3° C./min to 340° C., and holding for 3 hours. The catalyst compositions were allowed to cool under hydrogen to ambient temperature, after which they were stabilized by adding a flowing stream of 1% oxygen in nitrogen gas until the exotherm ceased. At no time was the exotherm allowed to exceed about 70° C.

The following examples were prepared using a process flow similar to that illustrated in FIG. 1. Ethylenediamine is pumped up to reaction pressure of 600-1000 psi and heated to a temperature of 140-160° C. Hydrogen mole percent (based on feed) from 0.1 to 10.0 is then added. The EDA hydrogen mixture is the feed upflow to a reactor containing ca. 274 grams of a heterogeneous Ni—Re (6.8:1.8 wt percent) catalyst on a 1/16" alumina silica (80:20) support. Reactor outlet product is sent to ammonia recovery to remove the feed H2 and the ammonia created in the process. The ammonia free material is then analyzed before being sent to a recovery system consisting of conventional distillation columns to recover EDA, PIP, DETA, TETA and Heavies. The data is presented as weight percents based on the total ethyleneamine content.

Example 1

Table 1 below shows the process is highly selective to DETA and TETA while keeping the level of cyclics (PIP, AEP, PEEDA) low. Also, the process can be operated at pressures from approximately 600 psia to 1000 psia at different EDA space velocities, hydrogen concentrations and temperatures while still maintaining good selectivity to acyclic products.

TABLE 1

| Reaction Conditions | | | | | | | | | | | | |
|---|---|---|---|---|---|---|---|---|---|---|---|---|
| T (° C.) | | 156.4 | 154.8 | 138.4 | 141.3 | 144.8 | 148.1 | 148.5 | 141.8 | 142.6 | 155.5 | 156.0 |
| P (psia) | | 615 | 615 | 815 | 815 | 815 | 815 | 815 | 1015 | 1015 | 1015 | 10 |
| H2, mole % in Feed | | 0.9 | 6.0 | 5.8 | 5.0 | 6.2 | 5.5 | 0.9 | 1.7 | 6.0 | 2.2 | 0.00 |
| SV EDA, gmol/hr/kgcat | | 27.2 | 27.8 | 14.7 | 14.3 | 14.4 | 15.3 | 15.9 | 10.1 | 25.2 | 9.6 | 27.0 |
| Feed (wt %) | EDA | 99.98 | 100.00 | 99.98 | 99.98 | 99.98 | 99.98 | 99.98 | 99.98 | 99.98 | 99.98 | 100.00 |
| | PIP | | | | | | | | | | | |
| | DETA | | | | | | | | | | | |
| | AEP | | | | | | | | | | | |
| | I-TETA | | | | | | | | | | | |
| | OTHER | 0.02 | 0.00 | 0.02 | 0.02 | 0.02 | 0.02 | 0.02 | 0.02 | 0.02 | 0.02 | 0.00 |
| Product composition (wt %) | EDA | 68.85 | 74.55 | 89.53 | 86.33 | 82.10 | 77.65 | 69.63 | 76.84 | 92.62 | 44.30 | 69.00 |
| (no NH3) | PIP | 4.14 | 2.30 | 0.34 | 0.53 | 0.98 | 1.62 | 4.06 | 1.66 | 0.17 | 12.50 | 3.00 |
| | DETA | 22.97 | 20.52 | 9.65 | 12.28 | 15.59 | 18.64 | 22.66 | 19.32 | 7.03 | 29.06 | 22.00 |
| | AEP | 0.27 | 0.10 | 0.01 | 0.01 | 0.02 | 0.05 | 0.24 | 0.05 | 0.00 | 1.38 | 0.00 |
| | I-TETA | 2.88 | 2.15 | 0.41 | 0.66 | 1.16 | 1.78 | 2.63 | 1.86 | 0.18 | 7.86 | 2.00 |
| | PEEDA | 0.09 | 0.05 | 0.01 | 0.00 | 0.01 | 0.02 | 0.11 | 0.02 | 0.00 | 0.99 | 0.00 |
| | I-TEPA | 0.30 | 0.18 | 0.01 | 0.03 | 0.08 | 0.17 | 0.22 | 0.18 | | 1.86 | 0.00 |
| | OTHER | 0.38 | 0.14 | 0.03 | 0.14 | 0.02 | 0.04 | 0.45 | 0.04 | 0.00 | 1.86 | 0.00 |
| EDA conversion, % | | 35.30 | 28.95 | 12.07 | 15.70 | 20.49 | 25.48 | 34.46 | 26.36 | 8.52 | 60.93 | 34.00 |
| Selectivity | | | | | | | | | | | | |
| DETA:PIP | | 5.6 | 8.9 | 28.3 | 23.1 | 15.9 | 11.5 | 5.6 | 11.6 | 43.2 | 2.3 | 5.0 |
| TETA:PIP | | 0.7 | 0.9 | 1.2 | 1.2 | 1.2 | 1.1 | 0.6 | 1.1 | 1.1 | 0.6 | 0.0 |
| (DETA + TETA)/PIP | | 6.2 | 9.8 | 29.3 | 24.2 | 17.0 | 12.6 | 6.2 | 12.7 | 43.6 | 3.0 | 6.0 |

Example 2

Table 2 below shows the results of feeding EDA/DETA over the heterogeneous catalyst. A higher level of TETA is produced as compared to an EDA only feed while still maintaining low levels of cyclic materials.

TABLE 2

| Reaction Conditions | | | | | | | | | |
|---|---|---|---|---|---|---|---|---|---|
| T (° C.) | | 148.1 | 148.5 | 151.3 | 153.6 | 147.6 | 149.1 | 151.7 | 154.0 |
| P (psia) | | 815 | 815 | 815 | 815 | 815 | 815 | 815 | 815 |
| H2, mole % in Feed | | 4.2 | 4.4 | 4.3 | 4.3 | 4.8 | 4.8 | 4.6 | 4.3 |
| SV EDA, gmol/hr/kgcat | | 13.5 | 13.4 | 13.6 | 13.5 | 12.4 | 12.6 | 12.7 | 13.2 |
| Feed (wt %) | EDA | 96.04 | 95.92 | 95.94 | 95.58 | 91.07 | 91.14 | 91.01 | 90.55 |
| | PIP | | | | | | | | |
| | DETA | 3.92 | 4.04 | 4.01 | 4.38 | 8.84 | 8.78 | 8.79 | 9.36 |
| | AEP | | | | | | | | |
| | I-TETA | | | | | | | | |
| | OTHER | 0.04 | 0.04 | 0.04 | 0.04 | 0.09 | 0.08 | 0.19 | 0.08 |
| Product composition (wt %) | EDA | 72.28 | 70.64 | 65.42 | 59.12 | 68.28 | 66.25 | 61.63 | 55.68 |
| (no NH3) | PIP | 2.30 | 2.63 | 3.88 | 5.84 | 2.89 | 3.42 | 4.71 | 6.76 |
| | DETA | 22.41 | 23.31 | 25.84 | 28.06 | 25.00 | 25.89 | 27.70 | 29.40 |
| | AEP | 0.10 | 0.12 | 0.20 | 0.38 | 0.16 | 0.19 | 0.29 | 0.49 |
| | I-TETA | 2.58 | 2.89 | 3.95 | 5.36 | 3.22 | 3.66 | 4.72 | 6.11 |
| | PEEDA | 0.02 | 0.03 | 0.05 | 0.11 | 0.03 | 0.04 | 0.07 | 0.15 |
| | I-TEPA | 0.23 | 0.28 | 0.47 | 0.80 | 0.32 | 0.40 | 0.63 | 0.99 |
| | OTHER | 0.04 | 0.06 | 0.13 | 0.26 | 0.07 | 0.10 | 0.18 | 0.34 |
| EDA conversion, % | | 32.60 | 34.39 | 40.36 | 47.19 | 38.91 | 41.43 | 46.87 | 53.56 |
| Selectivity | | | | | | | | | |
| DETA:PIP | | 8.0 | 7.2 | 5.6 | 4.0 | 5.5 | 4.9 | 3.9 | 2.9 |
| TETA:PIP | | 1.1 | 1.1 | 1.0 | 0.9 | 1.1 | 1.1 | 1.0 | 0.9 |
| (DETA + TETA)/PIP | | 10.9 | 10.0 | 7.7 | 5.7 | 9.8 | 8.6 | 6.9 | 5.3 |

Example 3

Table 3 below shows the results of feeding EDA/PIP over the heterogeneous catalyst. As compared to the table above, it can be seen that at similar EDA conversions, the DETA/PIP ratio is improved (Note: the PIP in the feed is subtracted from the PIP produced in the product).

TABLE 3

| Reaction Conditions | | | | | | | |
|---|---|---|---|---|---|---|---|
| T (° C.) | | 146.1 | 148.2 | 150.8 | 148.2 | 152.1 | 155.9 |
| P (psia) | | 815 | 815 | 815 | 815 | 815 | 815 |
| H2, mole % in Feed | | 4.0 | 4.5 | 4.1 | 4.3 | 4.3 | 4.4 |
| SV EDA, gmol/hr/kgcat | | 14.0 | 13.4 | 13.9 | 13.5 | 13.6 | 13.8 |
| Feed (wt %) | EDA | 98.54 | 98.54 | 98.55 | 96.43 | 96.37 | 96.37 |
| | PIP | 1.45 | 1.46 | 1.45 | 3.57 | 3.63 | 3.63 |
| | DETA | | | | | | |
| | AEP | | | | | | |
| | I-TETA | | | | | | |
| | OTHER | 0.00 | 0.00 | 0.00 | 0.00 | 0.00 | 0.00 |
| Product composition (wt %) | EDA | 78.03 | 73.45 | 68.71 | 71.64 | 63.76 | 53.93 |
| (no NH3) | PIP | 2.87 | 3.60 | 4.61 | 5.84 | 7.65 | 10.96 |
| | DETA | 17.47 | 20.47 | 23.08 | 20.06 | 24.15 | 27.35 |
| | AEP | 0.03 | 0.07 | 0.12 | 0.07 | 0.18 | 0.50 |
| | I-TETA | 1.45 | 2.16 | 3.04 | 2.14 | 3.65 | 5.76 |
| | PEEDA | 0.01 | 0.01 | 0.03 | 0.02 | 0.05 | 0.16 |
| | I-TEPA | 0.11 | 0.19 | 0.31 | 0.19 | 0.42 | 0.93 |
| | OTHER | 0.01 | 0.03 | 0.07 | 0.03 | 0.11 | 0.34 |
| EDA conversion, % | | 23.74 | 28.90 | 34.18 | 29.11 | 37.97 | 48.82 |
| Selectivity | | | | | | | |
| DETA:PIP | | 12.3 | 9.5 | 7.3 | 8.8 | 6.0 | 3.7 |
| TETA:PIP | | 1.0 | 1.0 | 1.0 | 0.9 | 0.9 | 0.8 |
| (DETA + TETA)/PIP | | 13.3 | 10.6 | 8.3 | 9.8 | 6.9 | 4.5 |

Note
DETA:PIP; TETA:PIP; and (DETA + TETA)/PIP calculated by subtracting PIP fed from PIP in the product mix

Example 4

Table 4 below shows the results of feeding EDA/TETA over the heterogeneous catalyst. Note that the DETA:PIP and TETA:PIP (Note that TETA is calculated by subtracting the TETA fed from TETA in the product mix) are improved over EDA only feed at similar EDA conversions. Additionally, more AEP is formed at similar EDA conversions.

TABLE 4

| Reaction Conditions | | | | | | | | | |
|---|---|---|---|---|---|---|---|---|---|
| T (° C.) | | 148.3 | 148.8 | 151.3 | 151.3 | 155.1 | 152.9 | 140.8 | 143.4 |
| P (psia) | | 815 | 815 | 815 | 815 | 815 | 815 | 815 | 815 |
| H2, mole % in Feed | | 5.7 | 4.6 | 4.5 | 4.3 | 4.7 | 4.0 | 3.9 | 4.0 |
| SV EDA, gmol/hr/kgcat | | 13.5 | 13.5 | 13.5 | 13.6 | 14.1 | 14.0 | 13.7 | 13.5 |
| Feed (wt %) | EDA | 95.80 | 95.80 | 95.80 | 95.80 | 95.80 | 95.90 | 95.90 | 95.83 |
| | PIP | | | | | | | | |
| | DETA | | | | | | | | |
| | AEP | | | | | | | | |
| | I-TETA | 4.06 | 4.06 | 4.06 | 4.07 | 4.07 | 3.93 | 3.93 | 4.01 |
| | OTHER | 0.14 | 0.14 | 0.14 | 0.13 | 0.13 | 0.16 | 0.16 | 0.17 |
| Product composition (wt %) | EDA | 73.93 | 71.09 | 65.64 | 65.53 | 55.85 | 60.58 | 82.21 | 78.93 |
| (no NH3) | PIP | 1.74 | 1.96 | 3.10 | 3.13 | 6.01 | 4.75 | 0.61 | 0.91 |
| | DETA | 17.45 | 19.80 | 22.69 | 22.75 | 26.44 | 24.72 | 12.11 | 14.67 |
| | AEP | 0.27 | 0.30 | 0.44 | 0.45 | 0.86 | 0.64 | 0.12 | 0.16 |
| | I-TETA | 5.36 | 5.50 | 6.28 | 6.29 | 7.90 | 7.01 | 4.32 | 4.57 |
| | PEEDA | 0.16 | 0.16 | 0.21 | 0.22 | 0.41 | 0.30 | 0.09 | 0.10 |
| | I-TEPA | 0.83 | 0.93 | 1.21 | 1.21 | 1.72 | 1.41 | 0.43 | 0.55 |
| | OTHER | 0.22 | 0.23 | 0.37 | 0.37 | 0.72 | 0.52 | 0.07 | 0.09 |
| EDA conversion, % | | 30.09 | 33.31 | 39.53 | 39.65 | 50.48 | 45.34 | 20.46 | 24.23 |
| Selectivity | | | | | | | | | |
| DETA:PIP | | 10.1 | 10.1 | 7.3 | 7.3 | 4.4 | 5.2 | 21.0 | 16.8 |
| TETA:PIP | | 0.7 | 0.7 | 0.7 | 0.7 | 0.6 | 0.6 | 0.6 | 0.6 |
| (DETA + TETA)/PIP | | 10.8 | 10.8 | 8.0 | 8.0 | 5.0 | 5.8 | 20.5 | 16.8 |

Example 5

Table 5 below shows the results of feeding EDA/AEP over the heterogeneous catalyst. As can be seen from the results, additional PEEDA is formed compared to EDA only feed at similar EDA conversions.

TABLE 5

| Reaction Conditions | | | | | | |
|---|---|---|---|---|---|---|
| T (° C.) | | 143.0 | 146.7 | 150.3 | 154.2 | 156.5 |
| P (psia) | | 815 | 815 | 815 | 815 | 815 |
| H2, mole % in Feed | | 4.1 | 3.9 | 4.5 | 4.2 | 4.2 |
| SV EDA, gmol/hr/kgcat | | 13.3 | 13.6 | 13.0 | 13.6 | 14.5 |
| Feed (wt %) | EDA | 96.25 | 96.24 | 96.24 | 96.25 | 96.24 |
| | PIP | | | | | |
| | DETA | | | | | |
| | AEP | 3.67 | 3.69 | 3.69 | 3.67 | 3.69 |
| | I-TETA | | | | | |
| | OTHER | 0.09 | 0.08 | 0.08 | 0.09 | 0.08 |
| Product composition (wt %) | EDA | 77.97 | 72.92 | 64.91 | 55.17 | 51.19 |
| (no NH3) | PIP | 0.98 | 1.74 | 3.36 | 6.20 | 7.84 |
| | DETA | 15.66 | 18.95 | 23.28 | 26.81 | 27.49 |
| | AEP | 3.77 | 3.76 | 3.85 | 4.15 | 4.31 |
| | I-TETA | 1.14 | 1.90 | 3.34 | 5.37 | 6.27 |
| | PEEDA | 0.35 | 0.47 | 0.67 | 0.98 | 1.16 |
| | I-TEPA | 0.07 | 0.16 | 0.37 | 0.83 | 1.09 |
| | OTHER | 0.04 | 0.07 | 0.18 | 0.43 | 0.58 |
| EDA conversion, % | | 21.68 | 27.51 | 36.61 | 47.42 | 51.73 |
| Selectivity | | | | | | |
| DETA:PIP | | 16.1 | 10.9 | 6.9 | 4.3 | 3.5 |
| TETA:PIP | | 1.2 | 1.1 | 1.0 | 0.9 | 0.8 |
| (DETA + TETA)/PIP | | 17.2 | 12.0 | 7.9 | 5.2 | 4.3 |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention.

What is claimed is:

1. A process for the manufacture of one or more ethyleneamines by a transamination reaction, comprising:

providing a first mixture comprising ethylenediamine and at least one additional ethyleneamine chosen from diethylenetriamine, triethylenetetramine, tetraethylenepentamine, piperazine, aminoethylethanolamine, aminoethylpiperazine, piperazinoethylethylenediamine, and heavy polyamine; and reacting the first mixture in the presence of a transamination catalyst to provide a second mixture comprising ethyleneamines, wherein at least two ethyleneamines are each present in a first amount in the first mixture, wherein the at least two ethyleneamines are each present in a second amount in the second mixture, and wherein the first amount is different than the second amount for each corresponding ethyleneamine of the at least two ethyleneamines.

2. The process according to claim 1, wherein the catalyst comprises:
   a) a support portion comprising an acidic mixed metal oxide comprising a transitional alumina and a second metal oxide; and
   b) a catalyst portion comprising nickel and rhenium, wherein:
   the second metal oxide has a weight percentage that is less than the weight percentage of alumina,
   the catalyst portion is 25 weight percent or less of the catalyst,
   the catalyst portion comprises nickel in an amount in the range of 2 to 20 weight percent, based upon total catalyst weight, and
   there is no boron in the catalyst portion.

3. The process of claim 1, wherein all of the ethyleneamines in the first mixture are present in an amount that is different than the amount of the corresponding ethyleneamines in the second mixture.

4. The process of claim 1, wherein the catalyst comprises:
   a) a support portion comprising an acidic mixed metal oxide comprising a transitional alumina and a second metal oxide, wherein the second metal oxide has a weight percentage that is less than the weight percentage of alumina; and
   b) a catalyst portion comprising one or more metals selected from the group consisting of cobalt, nickel, and copper,
   wherein there is no, or less than 0.01 wt. % rhenium in the catalyst, and the catalyst portion is 25 wt. % or less of the catalyst.

5. The process according to claim 4, wherein the catalyst portion is in the range of 3wt. % to 18 wt. % of the catalyst.

6. The process according to claim 4, wherein the catalyst portion comprises two or three metals selected from the group consisting of cobalt, nickel, and copper.

7. The process according to claim 6, wherein the catalyst portion comprises cobalt and nickel in a weight ratio in the range of 1:9 to 9:1.

8. The process according to claim 4, wherein the catalyst portion comprises no rhenium, or less than 0.005 wt. % rhenium.

9. A process for the manufacture of one or more ethyleneamines by a transamination reaction, comprising:
   providing a first mixture comprising ethylenediamine and at least one additional ethyleneamine chosen from diethylenetriamine, triethylenetetramine, tetraethylenepentamine, piterazine, aminoethylethanolamine, aminoethylpiperazine, piperazinoethylethylenediamine, and heavy polyamine; and
   reacting the first mixture in the presence of a transamination catalyst in a fixed bed reactor to provide a second mixture comprising ethyleneamines, wherein at least two ethyleneamines are each present in a first amount in the first mixture, wherein the at least two ethyleneamines are each present in a second amount in the second mixture, and wherein the first amount is different than the second amount for each corresponding ethyleneamine of the at least two ethyleneamines.

10. A process for the manufacture of one or more ethyleneamines by a transamination reaction, comprising:
    providing a first mixture comprising ethylenediamine and at least one additional ethyleneamine chosen from diethylenetriamine, triethylenetetramine, tetraethylenepentamine, piperazine, aminoethylethanolamine, aminoethylpiperazine, piperazinoethylethylenediamine, and heavy polyamine; and
    reacting the first mixture in the presence of a transamination catalyst to provide a second mixture comprising ethyleneamines, wherein at least two ethyleneamines are each present in a first amount in the first mixture, wherein the at least two ethyleneamines are each present in a second amount in the second mixture, wherein the first amount is different than the second amount for each corresponding ethyleneamine of the at least two ethyleneamines, and wherein the catalyst comprises:
    a) a support portion comprising an acidic mixed metal oxide comprising a transitional alumina and a second metal oxide; and
    b) a catalyst portion comprising nickel and rhenium, wherein:
    the second metal oxide has a weight percentage that is less than the weight percentage of alumina,
    the catalyst portion is 25 weight percent or less of the catalyst composition,
    the catalyst portion comprises nickel in an amount in the range of 2 to 20 weight percent, based upon total catalyst composition weight, and
    there is no boron in the catalyst portion.

11. The process according to claim 10, wherein the transitional alumina comprises delta alumina.

12. The process according to claim 11, wherein the transitional alumina further comprises one or more of gamma, theta or alpha alumina.

13. The process according to claim 12, wherein the support portion comprises at least 50 weight percent transitional phase alumina.

14. The process according to claim 10, wherein the transitional alumina comprises theta alumina.

15. The process according to claim 14, wherein the transitional alumina further comprises one or more of gamma or alpha alumina.

16. The process according to claim 1, wherein the second amount of at least one of the at least two ethyleneamines in the second mixture is greater than the first amount in the first mixture.

* * * * *

UNITED STATES PATENT AND TRADEMARK OFFICE
CERTIFICATE OF CORRECTION

PATENT NO. : 8,383,860 B2
APPLICATION NO. : 12/587372
DATED : February 26, 2013
INVENTOR(S) : Ronald G. Cook et al.

Page 1 of 1

It is certified that error appears in the above-identified patent and that said Letters Patent is hereby corrected as shown below:

In the Claims:

Column 13,
Line 56, "piterazine" should be --piperazine--

Signed and Sealed this
Twenty-eighth Day of May, 2013

Teresa Stanek Rea
*Acting Director of the United States Patent and Trademark Office*

UNITED STATES PATENT AND TRADEMARK OFFICE
CERTIFICATE OF CORRECTION

| | |
|---|---|
| PATENT NO. | : 8,383,860 B2 |
| APPLICATION NO. | : 12/587372 |
| DATED | : February 26, 2013 |
| INVENTOR(S) | : Ronald G. Cook et al. |

It is certified that error appears in the above-identified patent and that said Letters Patent is hereby corrected as shown below:

Title Page,
Inventors, "Thomas Z. Smack" should be --Thomas Z. Smak--

Signed and Sealed this
Thirtieth Day of June, 2015

Michelle K. Lee
*Director of the United States Patent and Trademark Office*